US00PP37265P2

(12) United States Plant Patent

Jacob Smit

(10) Patent No.: US PP37,265 P2
(45) Date of Patent: Feb. 10, 2026

(54) *MURDANNIA* PLANT NAMED 'EC-MURD-2504'

(50) Latin Name: *Murdannia loriformis*
Varietal Denomination: EC-MURD-2504

(71) Applicant: Eden Collection B.V., Sappemeer (NL)

(72) Inventor: Obed Jacob Smit, Sappemeer (NL)

(73) Assignee: Eden Collection B.V. (NL)

( * ) Notice: Subject to any disclaimer, the term of this patent is extended or adjusted under 35 U.S.C. 154(b) by 0 days.

(21) Appl. No.: 19/235,266

(22) Filed: Jun. 11, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./263.1, 373
CPC ... A01H 5/12; A01H 5/02; A01H 5/00; A01H 6/00
See application file for complete search history.

(56) References Cited

U.S. PATENT DOCUMENTS

PP31,588 P2 * 3/2020 van der Arend ..... A01H 5/02 Plt./373

* cited by examiner

*Primary Examiner* — June Hwu

(57) ABSTRACT

A new and distinct cultivar of *Murdannia* plant named 'EC-MURD-2504' is disclosed, characterized by compact plant habit, and fresh looking, elongated, white and dark green variegated leaves. The new cultivar is a *Murdannia*, typically produced as a container plant for ornamental purposes.

2 Drawing Sheets

Figure 1:
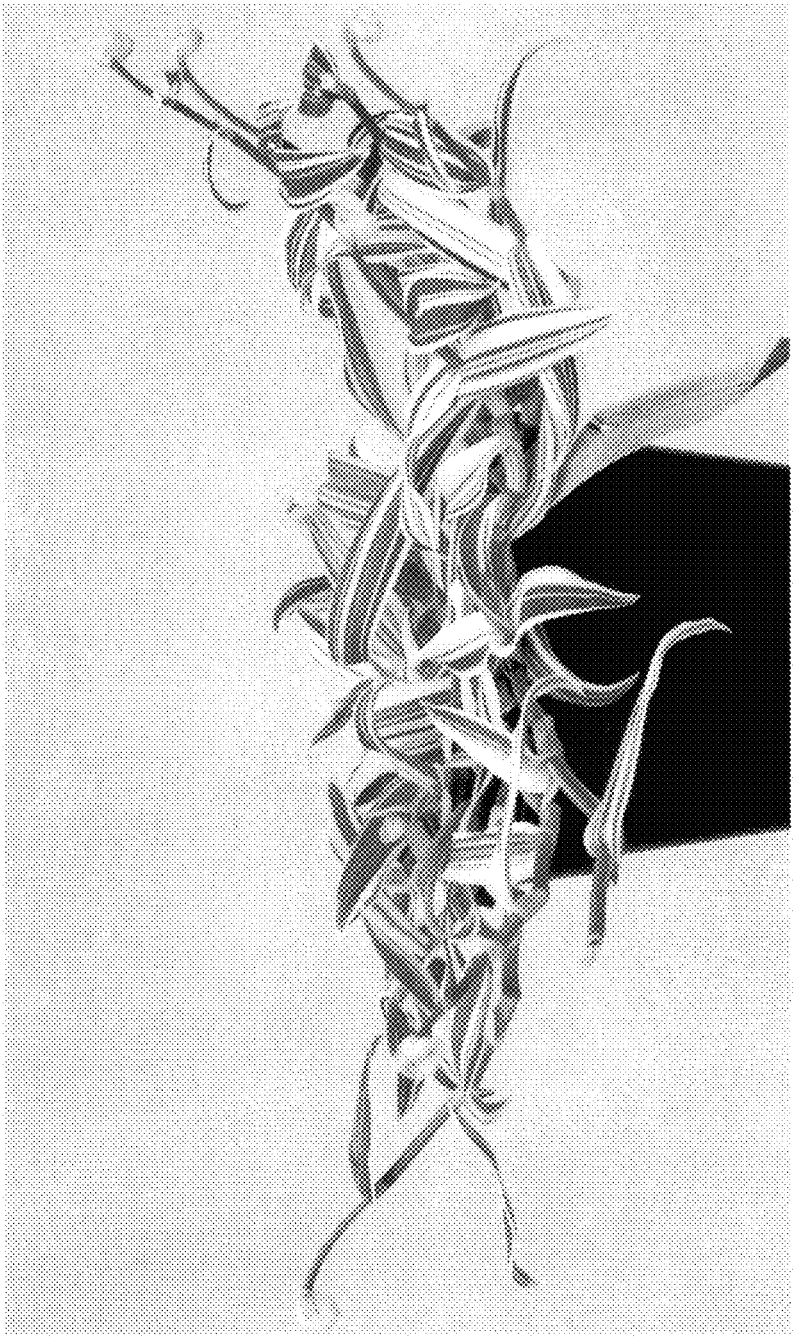
Figure 3:
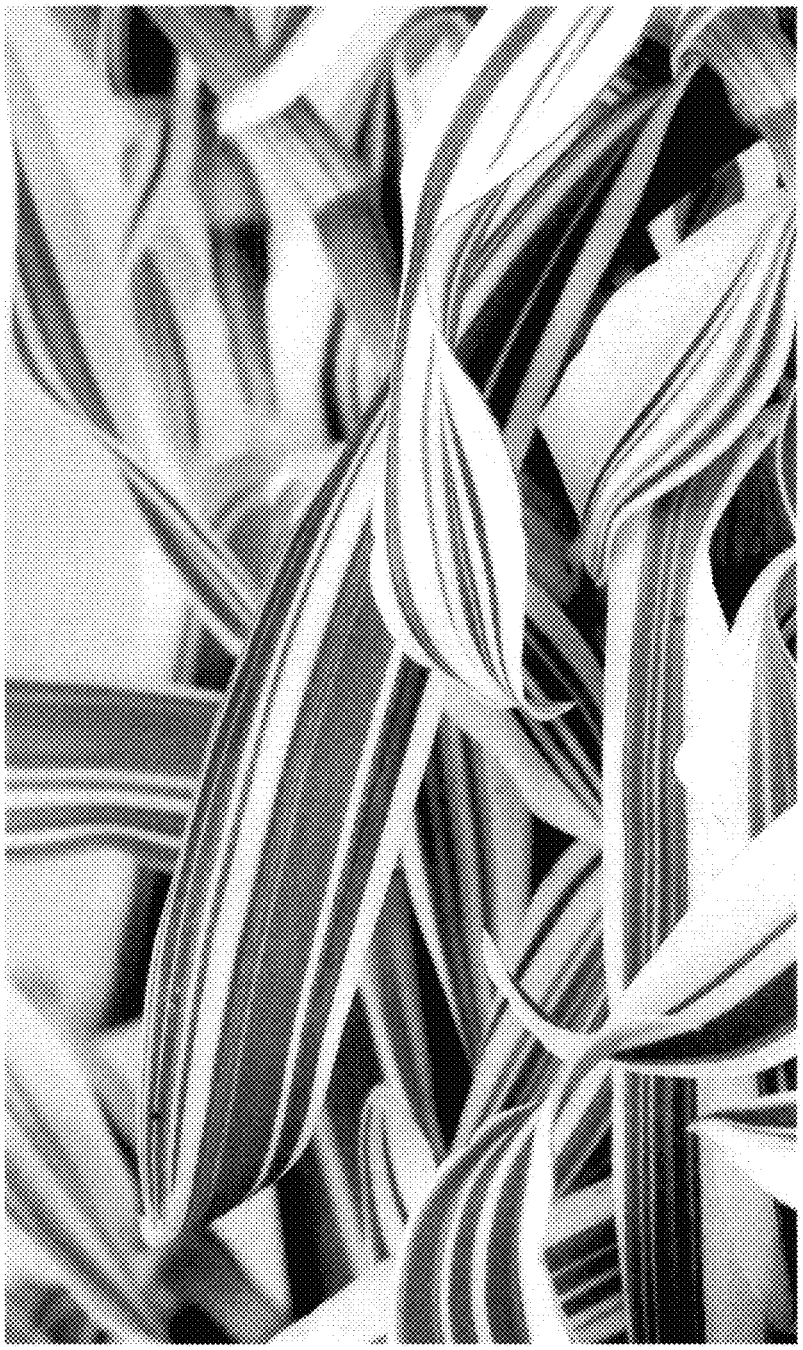

Latin name of the genus and species: *Murdannia loriformis.*

Cultivar denomination: 'EC-MURD-2504'.

BACKGROUND OF THE INVENTION

The new cultivar is a product of a planned breeding program to produce distinct and better performing *Murdannia* cultivars. The new cultivar was found by the inventor as a naturally-occurring branch mutation of *Murdannia loriformis*, the species itself. The discovery was made by the inventor, Obed J. Smit in May 2022, at a nursery in Sappemeer, the Netherlands.

Asexual reproduction of the new cultivar 'EC-MURD-2504' by top cuttings was first performed in Sappemeer, the Netherlands at a commercial greenhouse in April 2023, and has shown that the unique features of this cultivar are stable and reproduced true to type through successive generations.

SUMMARY OF THE INVENTION

The cultivar 'EC-MURD-2504' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'EC-MURD-2504'. These characteristics in combination distinguish 'EC-MURD-2504' as a new and distinct *Murdannia* cultivar:

1. Fresh looking, elongated white and dark green variegated leaves.
2. Compact plant habit.

PARENT COMPARISON

Plants of the new cultivar 'EC-MURD-2504' are similar to plants of the parent cultivar in most horticultural characteristics, however, plants of the new cultivar 'EC-MURD-2504' differ in the following characteristics:

1. Leaves of the new cultivar are variegated white and dark green, while the leaves of the parent are dark green without variegation.

COMMERCIAL COMPARISONS

Plants of the new cultivar 'EC-MURD-2504' are similar to plants of the commercial cultivar *Murdannia loriformis* 'PPIMUR004', U.S. Plant Pat. No. 31,588 also known as 'Bright Star'. However, plants of the new cultivar differ in the following characteristics:

1. Leaves of the new cultivar are variegated white and dark green, while the leaves of this comparator are grey-green with a dark green rim.
2. Plants of the new cultivar have a spreading habit of several branching shoots, while plants of this comparator have a rosette-like habit.
3. Leaves of the new cultivar are smaller and elongated, while leaves of this comparator are larger.

Plants of the new cultivar 'EC-MURD-2504' are similar to plants of the commercial cultivar *Tradescantia cerinthoides* 'EC-TRAD-2303', U.S. Plant Pat. No. 35,933. However, plants of the new cultivar differ in the following characteristics:

1. Leaves of the new cultivar are elongated with variegated white and dark green coloring, while the leaves of this comparator are more elliptical with lighter green and white stripes.

2. Plants of the new cultivar are more compact than plants of this comparator.
3. Plants of the new cultivar have shorter internodes than plants of this comparator.

BRIEF DESCRIPTION OF THE PHOTOGRAPHS

The accompanying photograph in FIG. 1 illustrates in full color a typical blooming plant of 'EC-MURD-2504' grown in a greenhouse. The plant is approximately 15 weeks of age.

FIG. 2 illustrates a close-up of the foliage.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2019 except where general terms of ordinary dictionary significance are used. The following observations and measurements describe 'EC-MURD-2504' plants at 15 weeks of age, grown in a greenhouse in April in Sappemeer, the Netherlands. The growing temperature ranged from 16° C. to 20° C. at night to 18° C. to 21° C. during the day. Measurements and numerical values represent averages of typical flowering types.

Botanical classification: *Murdannia loriformis* 'EC-MURD-2504'.

PROPAGATION

Time to initiate roots: About 10 days at 18° C. in summer; 14 days at 18° C. in winter.

Time to produce rooted cutting: About 25 days at 18° C. in summer; 33 days at 18° C. in winter.

Description of roots: Herbaceous, fine, moderately dense, freely branching. White in color, not accurately measured with R.H.S. chart.

PLANT

Plant type: Perennial potted plant.
Plant shape: Prostrate to flattened.
Growth habit: Spreading-creeping.
Plant spread: Approximately 26.4 cm.
Height: 9.4 cm to top of foliar plane; 11.6 cm to top of floral plane.
Growth rate: Moderate.
Plant vigor: Moderate to high.
Age of plant described: Approximately 15 weeks.
Branching habit: Basal branches with few lateral branches.
Pinching: Pinching not required.
Number of primary (main) branches per plant: Average 3.
Number of secondary (lateral) branches per plant: Average 4.
Main branches:
*Length*.—Average: 11.3 cm.
*Diameter*.—Average: 0.35 cm.
Internode length: Average: 2.6 cm.
Appearance and shape: Rounded.
Luster: Very slightly glossy.
Angle from vertical: Average 10°.
Strength: Strong.
Color:
*Developing*.—RHS Yellow-Green 144B, finely axially striped Green-White 157D.
*Mature*.—RHS Green 137A, finely axially striped White 155C.
*At Internodes*.—Internodes covered by leaf sheath; color under leaf sheath RHS Yellow-Green 145A, finely axially striped White 155C.
Pubescence: Stems moderately covered with a very short pubescence, average length of hairs: 0.2 mm, colored white, impossible to measure with RHS-17 CC due to small size.
Plant fragrance: None.

FOLIAGE

Leaf:
*Arrangement*.—Alternate, single.
*Quantity*.—Average 5.
*Average length*.—9.5 cm.
*Average width*.—1.7 cm.
*Shape of blade*.—Lanceolate.
*Whole leaf aspect*.—Slightly to moderately twisted, slightly curled downward, tip usually curled downward stronger, slightly leathery.
*Apex*.—Acute.
*Base*.—Sheathing. Sheath length: Average 0.8 cm. Sheath width: Average 0.5 cm. Sheath appearance: Moderately pubescent with very short, soft hairs, average length: 0.3 mm, colored transparent white; impossible to measure with RHS-CC due to small size. Sheath color: Transparent RHS White N155A and N155B, reticulately veined Yellow-Green 146C.
*Margin*.—Entire, slightly to moderately revolute.
*Undulation*.—Non-undulate to slightly coarsely undulate.
*Texture of top surface*.—Glabrous, smooth.
*Texture of bottom surface*.—Glabrous, smooth.
*Pubescence*.—At leaf base, margins at moderately pubescent, fading to non-pubescent at the apex, average length of hairs: 0.3 mm, colored transparent white; impossible to measure with RHS-CC due to small size.
*Luster, upper side*.—Slightly glossy.
*Luster, under side*.—Matte.
*Rugosity*.—Both sides non-rugose.
*Color*.—Young foliage upper side: RHS Green 137B and 141B, irregularly margined White NN155D and axillary striped Green 138C to 138D and White NN155B to NN155C. Young foliage under side: RHS Green 138B, irregularly margined White NN155C and NN155D, axillary striped Greyed-Green 190A, 191B, 191C, and White 155C. Mature foliage upper side: RHS Green 137B, NN137B and NN137C, irregularly margined White NN155C, axillary striped Green 138A, White 155C, Greyed-Green 191A and 191B. Mature foliage under side: RHS Greyed-Green 191A and 191B, irregularly margined White NN155C, axillary striped Greyed-Green 190A, 190B, 191C and White 155C.

*Venation*.—Pattern: Laciniate. Venation color upper side: Main vein RHS Green NN137B, secondary veins colored as lamina. Venation color under side: Main vein RHS Green 137C, secondary veins colored as lamina.

*Petiole*.—No petiole; leaves sheathing.

FLOWER

Inflorescence:

*Arrangement*.—Terminal raceme.

*Inflorescence type and form*.—Raceme.

*Inflorescence height*.—Average: 1.1 cm.

*Inflorescence diameter*.—Average: 0.8 cm.

*Quantity of flowers per inflorescence*.—Average: 6.

*Quantity of flowers per plant*.—None; flowers do not open but dry and fall off before opening.

*Quantity of flower buds per plant*.—Average 30.

*Natural flowering season*.—Year-round.

Flower bud:

*Flower bud length*.—0.4 cm.

*Flower bud diameter*.—0.15 cm.

*Flower bud shape*.—Obovate.

*Flower bud texture*.—Glabrous, smooth.

*Flower bud luster*.—Very slightly glossy.

*Flower bud color*.—RHS White N155A.

Flower: Flowers do not open, but dry and fall off before maturity.

Peduncles:

*Terminal peduncle length*.—Average 2 cm.

*Terminal peduncle diameter*.—Average 0.15 cm.

*Peduncle angle to lateral branch axis*.—Average angle 2.5°.

*Peduncle strength*.—Strong.

*Peduncle texture*.—Glabrous, smooth.

*Peduncle luster*.—Very slightly glossy.

*Peduncle color*.—RHS Green 137C, finely axially striped White 155C.

Pedicels:

*Length*.—0.15 cm.

*Width*.—0.5 mm.

*Angle*.—Average 30°.

*Strength*.—Moderate.

*Texture*.—Smooth, glabrous.

*Luster*.—Matte.

*Color*.—RHS Greyed-Green 197A.

Bracts:

*Shape*.—Orbicular, strongly concave.

*Apex*.—Obtuse.

*Base*.—Cuneate.

*Length*.—Average 0.8 cm.

*Diameter*.—Average 0.8 cm.

*Texture*.—Both sides smooth, glabrous, very slightly glossy.

*Color*.—Transparent RHS White N155A, reticulately veined Yellow-Green 143D.

REPRODUCTIVE ORGANS

Flowers do not open, but dry and are dropped before maturity. No reproductive structures are formed.

OTHER CHARACTERISTICS

Seeds and fruits: None observed to date.

Disease/pest resistance: No increased nor decreased resistance nor susceptibility to normal diseases and pests of *Murdannia* has been observed.

Temperature tolerance: Tolerates temperatures from 4° C. to 40° C. Hardy to USDA zones 11 to 13. Low to moderate tolerance to rain. Moderate to high tolerance to wind.

What is claimed is:

1. A new and distinct cultivar of *Murdannia* plant named 'EC-MURD-2504' as herein illustrated and described.

* * * * *